(12) United States Patent
    Bikumandla et al.

(10) Patent No.: US 12,616,386 B1
(45) Date of Patent: May 5, 2026

(54) INTEGRATED CIRCUIT FOR PHOTOPLETHYSMOGRAPHY (PPG)

(71) Applicant: Meta Platforms Technologies, LLC, Menlo Park, CA (US)

(72) Inventors: Manoj Bikumandla, Union City, CA (US); Andrew Matthew Bardagjy, Seattle, WA (US); Ajay Bikumandla, Union City, CA (US)

(73) Assignee: Meta Platforms Technologies, LLC, Menlo Park, CA (US)

( * ) Notice: Subject to any disclaimer, the term of this patent is extended or adjusted under 35 U.S.C. 154(b) by 1016 days.

(21) Appl. No.: 17/592,719

(22) Filed: Feb. 4, 2022

Related U.S. Application Data

(63) Continuation of application No. 17/217,672, filed on Mar. 30, 2021, now abandoned.

(51) Int. Cl.
| | |
|---|---|
| *A61B 5/024* | (2006.01) |
| *A61B 5/026* | (2006.01) |
| *A61B 5/0295* | (2006.01) |
| *A61B 5/1455* | (2006.01) |
| *G06F 3/01* | (2006.01) |

(Continued)

(52) U.S. Cl.
CPC ...... *A61B 5/02433* (2013.01); *A61B 5/02427* (2013.01); *A61B 5/0261* (2013.01); *A61B 5/0295* (2013.01); *A61B 5/14552* (2013.01); *H04N 23/45* (2023.01); *H04N 23/56* (2023.01); *G06F 3/011* (2013.01)

(58) Field of Classification Search
CPC ............ A61B 5/02433; A61B 5/02427; A61B 5/0261; A61B 5/0295; A61B 5/14552; H04N 23/45; H04N 23/56; G06F 3/011
See application file for complete search history.

(56) References Cited

U.S. PATENT DOCUMENTS

| | | | | |
|---|---|---|---|---|
| 2002/0038078 A1* | 3/2002 | Ito | .................. | A61B 5/14551 |
| | | | | 600/323 |
| 2003/0028085 A1* | 2/2003 | Al-Ali | ............... | A61B 5/14551 |
| | | | | 600/323 |

(Continued)

OTHER PUBLICATIONS

Gambino J., et al., "CMOS Image Sensor With High Refractive Index Lightpipe," International Electron Devices Meeting, Dec. 11-13, 2006, 4 pages.

(Continued)

*Primary Examiner* — Abid A Mustansir

(74) *Attorney, Agent, or Firm* — Freestone Intellectual Property Law PLLC; Aaron J. Visbeek

(57) ABSTRACT

In some embodiments, an apparatus comprises: a first die comprising one or more image sensors; a second die comprising one or more light emitters; one or more through package vias (TPVs), wherein a TPV of the one or more TPVs is configured to allow light emitted from at least one light emitter of the one or more light emitters to pass through the first die; and a controller. The controller may be configured to: cause the at least one light emitter to emit light, through the TPV of the one or more TPVs, toward a tissue of a user; determine one or more characteristics of reflected light captured by at least one image sensor of the one or more image sensors; and determine photoplethysmography (PPG) data for the user based on the determined one or more characteristics of the reflected light.

22 Claims, 9 Drawing Sheets

(51) Int. Cl.
  H04N 23/45   (2023.01)
  H04N 23/56   (2023.01)

(56)        References Cited

U.S. PATENT DOCUMENTS

| | | | | |
|---|---|---|---|---|
| 2016/0141440 | A1* | 5/2016 | Chun | H10F 55/255 |
| | | | | 257/82 |
| 2016/0356718 | A1* | 12/2016 | Yoon | H03M 3/464 |
| 2017/0164878 | A1 | 6/2017 | Connor | |
| 2020/0113507 | A1* | 4/2020 | Varghese | A61B 5/0077 |
| 2023/0204198 | A1* | 6/2023 | Pfeffer | H04N 23/56 |
| | | | | 362/227 |

OTHER PUBLICATIONS

Texas Instruments, "AFE4490 Integrated Analog Front End (AFE) for Pulse Oximeters," Retrieved on Mar. 30, 2021, 4 Pages, Retrieved from the Internet: URL: https://www.ti.com/product/AFE4490.
Texas Instruments, "Miniaturized Pulse Oximeter Reference Design," User's Guide and Test Report TIDA-00311, 2014 [Retrieved on Mar. 30, 2021], 24 pages, Retrieved from the Internet: URL: https://www.ti.com/lit/ug/tidu542/tidu542.pdf/tsM608663148939&&ref_url=https%3A%2F%2Fwww.bing.com%2F.
Texas Instruments, "SpO Pulse Ox Wrist Oximeter Reference Design," 2013, Retrieved on Mar. 30, 2021, 15 Pages, Retrieved from the Internet: URL: https://www.ti.com/lit/ug/tidul24/tidul24.pdf/tsM608620613495&&ref_url=https%3A%2F%2Fwww.ti.com%2Ftool%2FTIDA-00010.

* cited by examiner

200

202

204

206

208

210

212

600

800

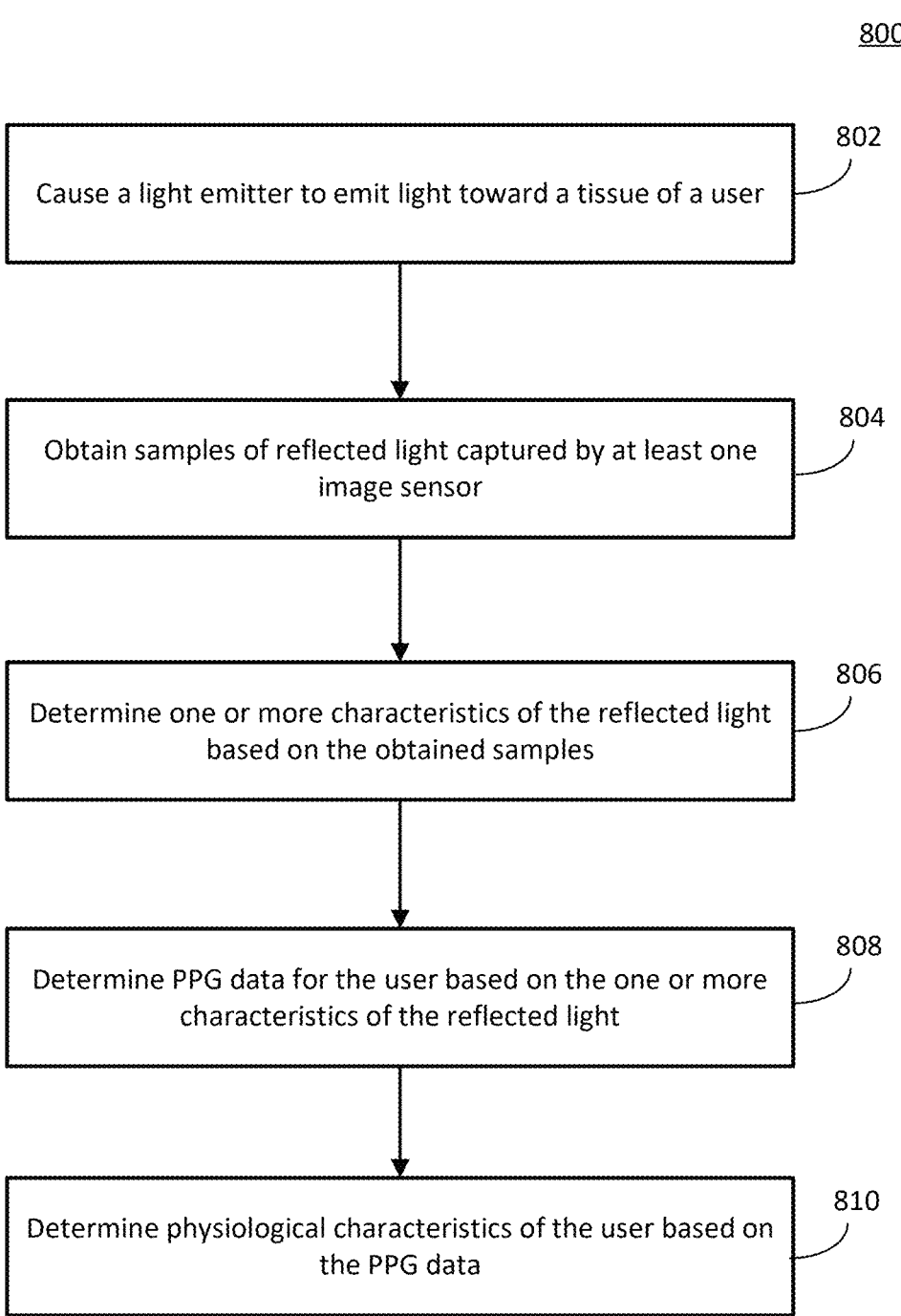

802

Cause a light emitter to emit light toward a tissue of a user

804

Obtain samples of reflected light captured by at least one image sensor

806

Determine one or more characteristics of the reflected light based on the obtained samples

808

Determine PPG data for the user based on the one or more characteristics of the reflected light

810

Determine physiological characteristics of the user based on the PPG data

FIG. 8

INTEGRATED CIRCUIT FOR PHOTOPLETHYSMOGRAPHY (PPG)

CROSS-REFERENCE TO RELATED APPLICATIONS

This application is a continuation of U.S. application Ser. No. 17/217,672, filed Mar. 30, 2021, titled "INTEGRATED CIRCUIT FOR PHOTOPLETHYSMOGRAPHY (PPG)," which is herein incorporated by reference in its entirety for all purposes.

BACKGROUND

Photoplethysmography (PPG) is a technique that is used to estimate various physiological characteristics of a user, such as heart rate, oxygen saturation, heart rate variability, etc. Conventional devices that perform PPG suffer from several drawbacks. For example, conventional devices may produce PPG data that is of poor quality due to being noisy or containing artifacts. For example, PPG data may be of poor quality due to ambient light incident on a light sensor used by a PPG device. Poor quality PPG data may produce inaccurate estimates of physiological characteristics. This may be problematic, because users of conventional PPG devices may rely on the PPG device to produce accurate estimates of physiological characteristics, for example, to monitor health conditions.

SUMMARY

This disclosure relates generally to an integrated circuit for photoplethysmography (PPG). According to certain embodiments, an apparatus may comprise: a first die comprising one or more image sensors; a second die comprising one or more light emitters; one or more through package vias (TPVs), wherein a TPV of the one or more TPVs is configured to allow light emitted from at least one light emitter of the one or more light emitters to pass through the first die; and a controller configured to: cause the at least one light emitter to emit light, through the TPV of the one or more TPVs, toward a tissue of a user; determine one or more characteristics of reflected light captured by at least one image sensor of the one or more image sensors; and determine photoplethysmography (PPG) data for the user based on the determined one or more characteristics of the reflected light.

In some embodiments, the TPV of the one or more TPVs is filled with a high-index light guide material such that the TPV couples light from the at least one light emitter.

In some embodiments, the apparatus may further comprise comprising a wire grid polarizer above the first die. In some embodiments, the wire grid polarizer comprises a plurality of orientations. In some embodiments, the wire grid polarizer is fabricated from a single mask, and wherein an orientation of the plurality of orientations is determined based on a portion of the single mask that has been etched away.

In some embodiments, the one or more light emitters comprise one or more edge vertical cavity surface-emitting lasers (e-VCSELs).

In some embodiments, at least a subset of the one or more light emitters emit light in an infrared wavelength. In some embodiments, the infrared wavelength is within a range of about 870 nanometers-970 nanometers.

In some embodiments, at least a subset of the one or more light emitters emit light in a red wavelength. In some embodiments, the red wavelength is within a range of about 630 nanometers to 680 nanometers.

In some embodiments, the one or more image sensors comprise one or more CMOS image sensors. In some embodiments, a CMOS image sensor of the one or more CMOS image sensors comprises two transfer gates. In some embodiments, causing the one or more light emitters to emit light towards the tissue of the user comprises causing the one or more light emitters to emit light as a pulsed waveform having a predetermined frequency, and the controller is further configured to: receive a first set of samples associated with a first transfer gate of the two transfer gates by activating and deactivating the first transfer gate of the two transfer gates with a first waveform having the predetermined frequency and in phase with the pulsed waveform; and receive a second set of samples associated with a second transfer gate of the two transfer gates by activating and deactivating the second transfer gate of the two transfer gates with a second waveform having the predetermined frequency and 90 degrees out of phase with the pulsed waveform. In some embodiments, the controller is further configured to determine a DC offset of the PPG data based on an average of two samples of the first set of samples. In some embodiments, the controller is further configured to determine a phase of the PPG data based on a ratio of a sample of the first set of samples to a sample of the second set of samples. In some embodiments, a CMOS image sensor of the one or more CMOS image sensors is a 4T CMOS image sensor.

According to some embodiments, an apparatus may comprise: one or more image sensors; a wire grid polarizer associated with the one or more image sensors; one or more light emitters; a wire grid polarizer associated with the one or more light emitters; and a controller. The controller may be configured to: cause at least one light emitter of the one or more light emitters to emit light toward a tissue of a user; determine one or more characteristics of reflected light captured by at least one image sensor of the one or more image sensors; and determine photoplethysmography (PPG) data for the user based on the determined one or more characteristics of the reflected light.

In some embodiments, the one or more image sensors comprise one or more CMOS image sensors. In some embodiments, a CMOS image sensor of the one or more CMOS image sensors comprises two transfer gates. In some embodiments, causing the at least one light emitter to emit light toward the tissue of the user comprises causing the one or more light emitters to emit light as a pulsed waveform having a predetermined frequency, and the controller is further configured to: activate and deactivate a first transfer gate of the two transfer gates with a first waveform having the predetermined frequency and in phase with the pulsed waveform; and activate and deactivate a second transfer gate of the two transfer gates with a second waveform having the predetermined frequency and 90 degrees out of phase with the pulsed waveform.

According to some embodiments, a method comprises: causing at least one light emitter to emit light toward a tissue of a user, wherein a first die comprises the at least one light emitter, and wherein light emitted from the at least one light emitter passes through one or more through package vias (TPVs) and through a second die that comprises one or more image sensors; determining one or more characteristics of reflected light captured by at least one image sensor of the one or more image sensors; and determining photoplethysmography (PPG) data for the user based on the determined one or more characteristics of the reflected light.

In some embodiments, causing the one or more light emitters to emit light towards the tissue of the user comprises causing the one or more light emitters to emit light as a pulsed waveform having a predetermined frequency, and the method further comprises: receiving a first set of samples associated with a first transfer gate of the two transfer gates by activating and deactivating the first transfer gate of the two transfer gates with a first waveform having the predetermined frequency and in phase with the pulsed waveform; and receiving a second set of samples associated with a second transfer gate of the two transfer gates by activating and deactivating the second transfer gate of the two transfer gates with a second waveform having the predetermined frequency and 90 degrees out of phase with the pulsed waveform. In some embodiments, the method further comprises determining a DC offset of the PPG data based on an average of two samples of the first set of samples. In some embodiments, the method further comprises determining a phase of the PPG data based on a ratio of a sample of the first set of samples to a sample of the second set of samples.

According to some embodiments, an apparatus comprises: means for causing at least one light emitter to emit light toward a tissue of a user, wherein a first die comprises the at least one light emitter, and wherein light emitted from the at least one light emitter passes through one or more through package vias (TPVs) and through a second die that comprises one or more image sensors; means for determining one or more characteristics of reflected light captured by at least one image sensor of the one or more image sensors; and means for determining photoplethysmography (PPG) data for the user based on the determined one or more characteristics of the reflected light.

According to some embodiments, a non-transitory computer-readable medium stores instructions for: causing at least one light emitter to emit light toward a tissue of a user, wherein a first die comprises the at least one light emitter, and wherein light emitted from the at least one light emitter passes through one or more through package vias (TPVs) and through a second die that comprises one or more image sensors; determining one or more characteristics of reflected light captured by at least one image sensor of the one or more image sensors; and determining photoplethysmography (PPG) data for the user based on the determined one or more characteristics of the reflected light.

This summary is neither intended to identify key or essential features of the claimed subject matter, nor is it intended to be used in isolation to determine the scope of the claimed subject matter. The subject matter should be understood by reference to appropriate portions of the entire specification of this disclosure, any or all drawings, and each claim. The foregoing, together with other features and examples, will be described in more detail below in the following specification, claims, and accompanying drawings.

BRIEF DESCRIPTION OF THE DRAWINGS

Illustrative embodiments are described in detail below with reference to the following figures.

FIG. 8 is a flowchart of an example process that can be used to determine PPG data and/or physiological characteristics based on PPG data according to certain embodiments.

Figure 1A:
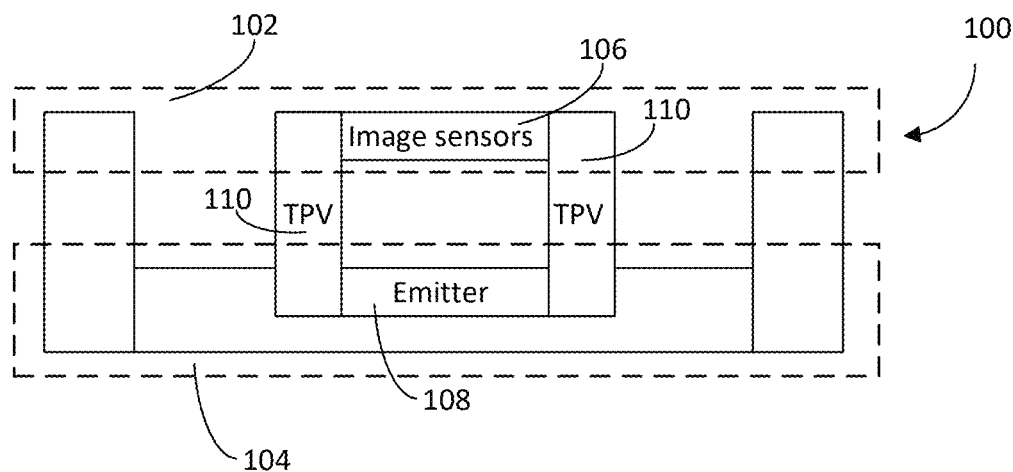
FIGS. 1A and 1B are simplified schematic diagrams that show a side view and a top view, respectively, of an example integrated circuit for photoplethysmography (PPG) in a stacked configuration according to certain embodiments.

The figures depict embodiments of the present disclosure for purposes of illustration only. One skilled in the art will readily recognize from the following description that alternative embodiments of the structures and methods illustrated may be employed without departing from the principles, or benefits touted, of this disclosure.

In the appended figures, similar components and/or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

This disclosure relates generally to integrated circuits for photoplethysmography (PPG). More specifically, and without limitation, disclosed herein are various integrated circuits that can be used for determining PPG data and/or physiological characteristics of a user based on PPG data and techniques for determining PPG data and/or physiological characteristics of a user based on PPG data using such integrated circuits. Various inventive embodiments are described herein, including devices, systems, methods, materials, and the like.

PPG is used to non-invasively estimate various physiological characteristics of a user, such as heart rate, heart rate variability, oxygen saturation, blood pressure, and the like. Conventional devices that perform PPG typically have one or more light emitters that emit light toward a tissue of the user, one or more light sensors that detect incident light (e.g., reflected from the tissue of the user or within internal elements of a body of the user proximal to the tissue of the user), and a computational block that determines PPG data or physiological characteristics of the user based on the PPG data. The light emitter(s), light sensor(s), and computational block are typically discrete components that are packaged separately. Use of discrete components that are packaged separately has several disadvantages. For example, using separate components that are packaged separately increases form factor. Increased form factor is problematic in instances in which a PPG device is to be incorporated in wearable devices. Additionally, increased form factor limits the number of light sensors or light emitters that can be used. Use of discrete components that are packaged separately may also increase testing time, because each separately packaged component must be tested and calibrated separately.

Moreover, using a conventional PPG device, it can be difficult to distinguish ambient background light from a light signal of interest (e.g., light reflected from tissue of a user), both of which may be incident on the light sensor(s). Inability to distinguish or separate ambient background light from a light signal of interest is problematic, particularly in instances in which a PPG device is to be used in bright environments, (e.g., outside, in a well-lit room, or the like).

The devices, systems, methods, materials, and the like described herein include various integrated circuit packages that incorporate one or more light sensors, one or more light emitters, and at least one processor in a single package, thereby reducing form factor and reducing testing time. Moreover, the devices, systems, methods, materials, and the like described herein include techniques for utilizing phase and/or polarization information associated with incident light on one or more light sensors. Use of phase information allows ambient light to be filtered, rejected, or otherwise separated from detected light signals of interest (e.g., light reflected from tissue of a user, or the like). Use of polarization information allows various body elements to be segmented or discriminated. For example, use of polarization information allows light signals reflected from a particular layer of skin to be separated from light signals reflected from other layers of skin, light signals reflected from skin to be separated from light signals reflected from bone, and the like.

According to certain embodiments, one or more light emitters and one or more light sensors may be packaged such that the one or more light emitters and the one or more light sensors are stacked vertically. For example, in some embodiments, the one or more light sensors may be fabricated on a first die of an integrated circuit, and the one or more light emitters may be fabricated on a second die of the integrated circuit. The first die and the second die may be fabricated such that the first die and the second die are stacked vertically. In some embodiments, the integrated circuit may have one or more through package vias (TPVs). Each TPV may be configured to allow light emitted from at least one light emitter to pass through the first die (that includes one or more light sensors) prior to being directed toward the tissue of the user. In some embodiments, each TPV may be filled with a high-index light guide material such that the TPV couples light from at least one light emitter. Examples of vertically stacked light emitters and light sensors are shown in and described below in connection with FIGS. 1A and 1B.

In some embodiments, one or more light emitters and one or more light sensors (which may be stacked vertically, as described above) may be packaged with an integrated circuit that includes a processor for determining PPG data based on characteristics of reflected light detected by the one or more light sensors. In some embodiments, the processor may be part of an application specific integrated circuit (ASIC). In some embodiments, the processor may be an advanced RISC machine (ARM), an x86 processor, or the like. In some embodiments, the components may be laid out in a package where the components are laid out side-by-side, as shown in and described below in connection with FIG. 9A. In some embodiments, the components may be laid out in a package where the components are stacked vertically, as shown in and described below in connection with FIG. 9B.

Polarizing light detected by one or more image sensors may be useful in segmenting or discriminating detected light reflected from various body elements (e.g., skin, particular layers of skin, bone, blood vessels, or the like). However, polarizing only detected light may result in a decrease in signal to noise ratio (SNR). Accordingly, it may be beneficial to polarize both emitted light and detected light. In some embodiments, a wire grid polarizer may be used to polarize light incident on one or more light sensors and light emitted by one or more light emitters toward tissue of a user with the same orientation. For example, in embodiments in which one or more light sensors and one or more light emitters are stacked vertically, a wire grid polarizer may be fabricated above a first die that includes the one or more light sensors. Continuing with this example, light emitted by one or more light emitters included in a second die may pass through the wire grid polarizer prior to being directed toward the tissue of the user.

In some embodiments, image sensors described herein may be complementary metal-oxide-semiconductor (CMOS) image sensors. For example, in some embodiments, an image sensor may be a 4T CMOS image sensor with four transistors, including transfer, reset, and source follower gates. An example of a 4T CMOS image sensor is shown in and described below in connection with FIG. 4.

As another example, in some embodiments, an image sensor may be a lock-in pixel CMOS image sensor with two transfer gates. An example of a lock-in pixel CMOS image sensor is shown in and described below in connection with FIG. 5. Use of a lock-in pixel CMOS image sensor may allow phase characteristics of detected light to be determined. For example, in some embodiments, quadrature sampling may be performed using the two transfer gates of the lock-in pixel CMOS image sensor. As a more particular example, in some embodiments, the two transfer gates may be activated and deactivated with waveforms that are 90 degrees out of phase from each other. Continuing further with this particular example, in some embodiments, phase characteristics may be determined based on ratios of detected light measurements from the two transfer gates, as shown in and described below in connection with FIG. 7.

The integrated circuits described herein may be used in conjunction with various technologies, such as an artificial reality system. An artificial reality system, such as a head-mounted display (HMD) or heads-up display (HUD) system, generally includes a display configured to present artificial images that depict objects in a virtual environment. The display may present virtual objects or combine images of real objects with virtual objects, as in virtual reality (VR), augmented reality (AR), or mixed reality (MR) applications. For example, in an AR system, a user may view both displayed images of virtual objects (e.g., computer-generated images (CGIs)) and the surrounding environment by, for example, seeing through transparent display glasses or lenses (often referred to as optical see-through) or viewing displayed images of the surrounding environment captured by a camera (often referred to as video see-through). In some AR systems, the artificial images may be presented to users using an LED-based display subsystem.

In some embodiments, the integrated circuits or integrated circuit packages described herein may be integrated into an HMD. For example, such an HMD may include one or more light emitters and/or one or more light sensors incorporated into a portion of a frame of the HMD such that light can be emitted toward a tissue of a wearer of the HMD that is proximate to or touching the portion of the frame of the HMD. Example locations of such a portion of a frame of an HMD may include a portion configured to be proximate to an ear of the wearer (e.g., proximate to a superior tragus, proximate to a superior auricular, proximate to a posterior auricular, proximate to an inferior auricular, or the like), proximate to a forehead of the wearer, or the like. It should be noted that multiple sets of light emitters and light sensors may be incorporated into a frame of an HMD such that PPG can be determined from measurements associated with multiple body locations of a wearer of the HMD.

In the following description, for the purposes of explanation, specific details are set forth in order to provide a thorough understanding of examples of the disclosure. However, it will be apparent that various examples may be practiced without these specific details. For example, devices, systems, structures, assemblies, methods, and other components may be shown as components in block diagram form in order not to obscure the examples in unnecessary detail. In other instances, well-known devices, processes, systems, structures, and techniques may be shown without necessary detail in order to avoid obscuring the examples. The figures and description are not intended to be restrictive. The terms and expressions that have been employed in this disclosure are used as terms of description and not of limitation, and there is no intention in the use of such terms and expressions of excluding any equivalents of the features shown and described or portions thereof. The word "example" is used herein to mean "serving as an example, instance, or illustration." Any embodiment or design described herein as "example" is not necessarily to be construed as preferred or advantageous over other embodiments or designs.

In some embodiments, one or more image sensors and one or more light emitters may be stacked vertically. A vertically stacked configuration may allow for a smaller form factor by allowing the one or more image sensors and the one or more light emitters to share the same x-y space. In some embodiments, the one or more image sensors may be fabricated as part of a first die of an integrated circuit. In some embodiments, the one or more light emitters may be fabricated as part of a second die of the integrated circuit. In some such embodiments, the first die and the second die may be stacked vertically.

In some embodiments, one or more TPVs may be drilled through a first die that includes one or more image sensors to a second die that includes one or more light emitters. Accordingly, light emitted by the one or more light emitters may pass through the first die via the one or more TPVs. In some embodiments, a TPV may be filled with a high-index light guide such that the TPV couples light from at least one light emitter.

Figure 1B:
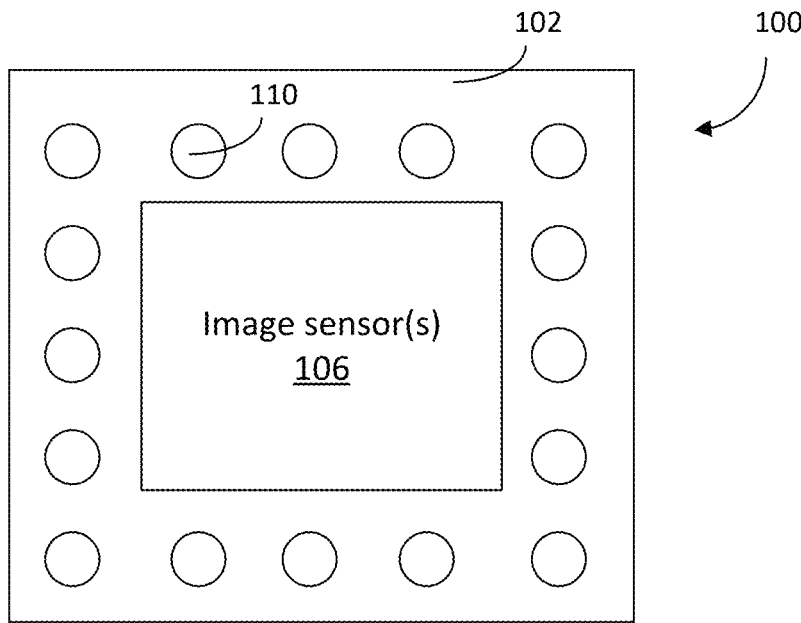

FIGS. 1A and 1B show simplified schematic diagram 100 that illustrate portions of an example integrated circuit for PPG that includes one or more light emitters and one or more light sensors in a stacked configuration according to certain embodiments.

Referring to FIG. 1A, schematic diagram 100 includes a first die 102 and a second die 104. In some embodiments, as shown in FIG. 1A, first die 102 may be above second die 104. For example, in some embodiments, first die 102 and second die 104 may be stacked.

First die 102 may include image sensor(s) 106. In some embodiments, image sensor(s) 106 may be CMOS image sensors. For example, in some embodiments, on or more of image sensor(s) 106 may be 4T CMOS image sensors, as shown in and described below in connection with FIG. 4. As another example, in some embodiments, one or more of image sensor(s) 106 may be CMOS image sensors with two transfer gates, as shown in and described below in connection with FIG. 5. It should be noted that CMOS image sensors with two transfer gates are generally referred to as "lock-in pixel CMOS image sensors" herein.

It should be noted that image sensor(s) 106 may include any suitable number (e.g., one, twenty, 64, 4,096, or the like) of image sensors arranged in any suitable pattern. For example, image sensor(s) 106 may be arranged in a rectangle, in a square, in a hexagon, or the like. As a more particular example, in some embodiments, image sensor(s) 106 may include an array (e.g., an 8×8 array, a 10×10 array, a 16×16 array, a 24×24 array, a 64×64 array, a 100×100 array, a 32×4 array, a 10×6 array, or the like) of image sensors. Example dimensions of an image sensor may be 10 micrometers×10 micrometers, 15 micrometers×15 micrometers, or the like. Accordingly, in an instance in which image sensor(s) 106 corresponds to a 64×64 array of image sensors each having dimensions of 10 micrometers×10 micrometers, image sensor(s) 106 may collectively have a dimension of about 640 micrometers×640 micrometers.

Second die 104 may include one or more light emitters 108. In some embodiments, light emitters of one or more light emitters 108 may be a semiconductor laser diode. Examples of types of semiconductor laser diodes that may be used include: vertical cavity surface-emitting lasers (VCSELs), such as edge-emitting VCSELs; vertical-external cavity surface-emitting lasers (VECSELs); distributed Bragg reflector lasers; and the like. In some embodiments, light emitters of one or more light emitters 108 may be LEDs.

In some embodiments, light emitters of light emitters 108 may emit light of any suitable wavelength. For example, in some embodiments, light within an infrared wavelength may be emitted. Emitted infrared light may be within a range of about 870 nanometers-1000 nanometers, within a range of about 870 nanometers-970 nanometers, within a range of about 920 nanometers-970 nanometers, or the like. As another example, in some embodiments, light within a red wavelength may be emitted. Emitted red wavelength light may be within a range of about 580 nanometers-700 nanometers, within a range of about 630 nanometers-680 nanometers, or the like.

In some embodiments, light emitters of light emitters 108 may be pulsed. The light emitters may be pulsed at a predetermined frequency. In some embodiments, the pulsed frequency may be in the kHz range, e.g., 3 kHz, 5 khZ, 8 khZ, 10 kHz, or the like. In some embodiments, two light emitters of light emitters 108 may be pulsed out of phase from each other or in phase with each other.

As shown in FIG. 1A, in some embodiments, one or more TPVs 110 may be configured to allow light emitted from at least one light emitter of light emitters 108 to pass through first die 102. In some embodiments, each TPV of TPVs 110 may be a hole drilled through first die 102. In some embodiments, each TPV of TPVs 110 may be filled with a high-index light guide material. In some embodiments, the high-index light guide material may be silicon-based. Silicon-based materials may be ideal due to a bandgap on the order of 1.1 eV. Examples of a high-index light guide material that may be used include silicon nitride, silicon trinitride, or similar materials, as described in "CMOS image sensor with high refractive index lightpipe" by J. Gambino, B. Leidy, A. Watts, C. Musante, K. Ackerson, S. Mongeon, J. Adkisson, R. J. Rassel, K. Ogg, J. Ellis-Monaghan, M. Jaffe, M. Laukkanen, K. Karaste, W. Mclaughlin, T. Gädda, J. Rantala in Proc. Of 2009 International Image Sensor Workshop, Bergen, NORWAY, Jun. 22-28, 2009, which is hereby incorporated by reference herein in its entirety. It should be noted that each TPV of TPVs 110 may be at a position of first die 102 at which there are no image sensors of image sensors 106. In other words, each TPV of TPVs 110 may be positioned at a portion of first die 102 that corresponds to a "dead zone" of first die 102. In some embodiments, a TPV may have a diameter within a range of about 100-200 micrometers.

FIG. 1B shows a top view of schematic diagram 100. As illustrated in FIG. 1B, one or more TPVs 110 are shown at various positions of first die 102. Note that, as described above in connection with FIG. 1A, the one or more TPVs 110 are positioned at locations of first die 102 for which no image sensors are positioned. Additionally, it should be noted that second die 104 (and consequently, light emitters of one or more light emitters 108) are not visible in the top view shown in FIG. 1B.

Polarizing detected light prior to capture by one or more light sensors may allow for separation of various internal elements within a body part on which PPG is being performed. For example, polarization of reflected light may allow for separation of light signals reflected off a first layer of skin from light reflected off other layers of skin, separation of light reflected off skin from light reflected off bone, and the like. Polarization of light that is captured by the one or more image sensors may therefore improve algorithms that determine physiological characteristics using the characteristics of the reflected light.

However, polarizing only the detected light may reduce SNR by effectively reducing the amount of reflected light detected by the image sensors. By polarizing emitted light with the same polarization as the reflected light that is detected by the image sensors, the SNR may effectively be increased.

In some embodiments, both the emitted light and the detected light may be polarized in conjunction with each other using a wire grid polarizer. For example, in some embodiments in which a first die including one or more image sensors is stacked on a second die including one or more light emitters with one or more TPVs allowing light from the one or more light emitters to pass through the first die, a wire grid polarizer may be used to polarize both emitted light as well as reflected light detected by the one or more image sensors. As a more particular example, a wire grid polarizer can be applied above the first die, thereby polarizing reflected light that is detected by the one or more image sensors. Continuing with this more particular example, emitted light from one or more light emitters included in the second die may be polarized prior to being directed toward tissue of a subject, because the emitted light will pass through the first die as well as the wire grid polarizer above the first die.

In some embodiments, a wire grid polarizer may have multiple orientations, each having any suitable polarization angle. In some embodiments, a wire grid polarizer that includes polarizations of multiple orientations may be fabricated from a single mask. For example, in some embodiments, the single mask may include the multiple orientations. Continuing with this example, a polarization orientation applicable to a corresponding portion of a first die may be determined based on a portion of the mask that has been etched away.

Figure 2:
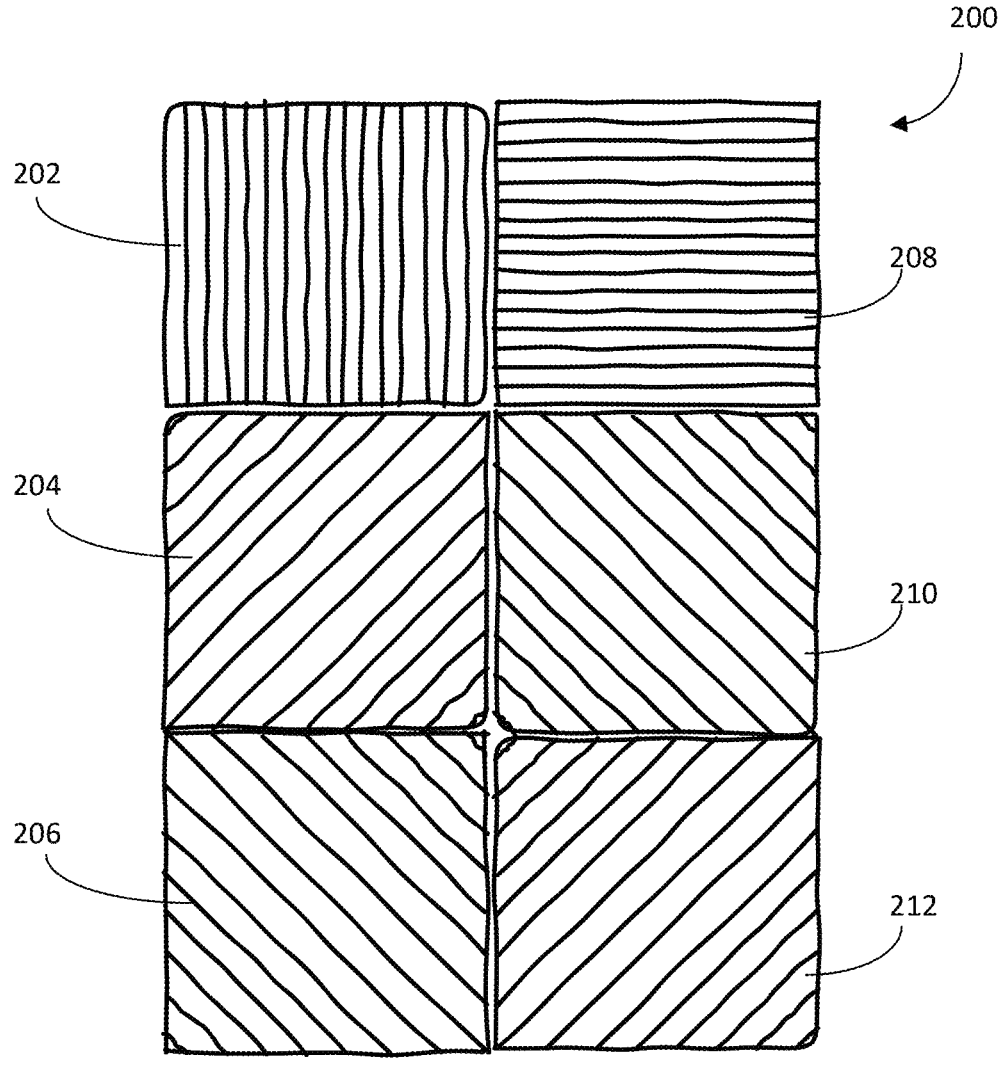
FIG. 2 is a simplified schematic diagram of an example wire grid polarizer that can be used in connection with an integrated circuit for PPG according to certain embodiments.

FIG. 2 shows a schematic diagram of a wire grid polarizer 200 having multiple orientations according to some embodiments.

In some embodiments, wire grid polarizer 200 may have multiple portions, each associated with a different polarization angle. For example, wire grid polarizer 200 has portions 202, 204, 206, 208, 210, and 212, each associated with a different polarization angle.

Each portion of wire grid polarizer 200 may have metal lines that are formed on a substrate. In some embodiments, each metal line may have a pitch, a width, and a height. In some embodiments, a pitch of a metal line may be within a range of 100 nanometers to 250 nanometers. In some embodiments, a width of a metal line may be within a range of about 100 nanometers to 250 nanometers. In some embodiments, a height of a metal line may be within a range of about 100 nanometers to 250 nanometers. The pitch, width, and/or the height of the metal lines may be dependent on the wavelength of light that is to be polarized. In some embodiments, a metal line may have a high aspect ratio such that a height of a metal line is greater than a width of the metal line. In some embodiments, a wire grid polarizer may be an off-the-shelf wire grid polarizer, such as a wire grid polarizer from THORLABS, or the like.

As illustrated in FIG. 2, within each portion of wire grid polarizer 200, the metal lines may be separated and parallel with each other. An angle of the lines determines a polarization angle associated with the portion of wire grid polarizer. For example, with respect to light incident on a particular portion of wire grid polarizer 200, a first component of the incident light parallel to the lines in the portion of wire grid polarizer 200 is reflected, and a second component of the incident light perpendicular to the metal lines is transmitted through wire grid polarizer 200. Accordingly, portion 202 of wire grid polarizer may allow incident light to be transmitted that is substantially perpendicular or orthogonal to incident light that is transmitted through portion 208 of wire grid polarizer.

In some embodiments, wire grid polarizer 200 may be formed with a substrate using a single mask. In some embodiments, a portion of the mask that is etched away for a corresponding portion of wire grid polarizer 200 determines an orientation (that is, angle) of the metal lines that determine a polarization angle of the corresponding portion of wire grid polarizer 200.

Figure 3:
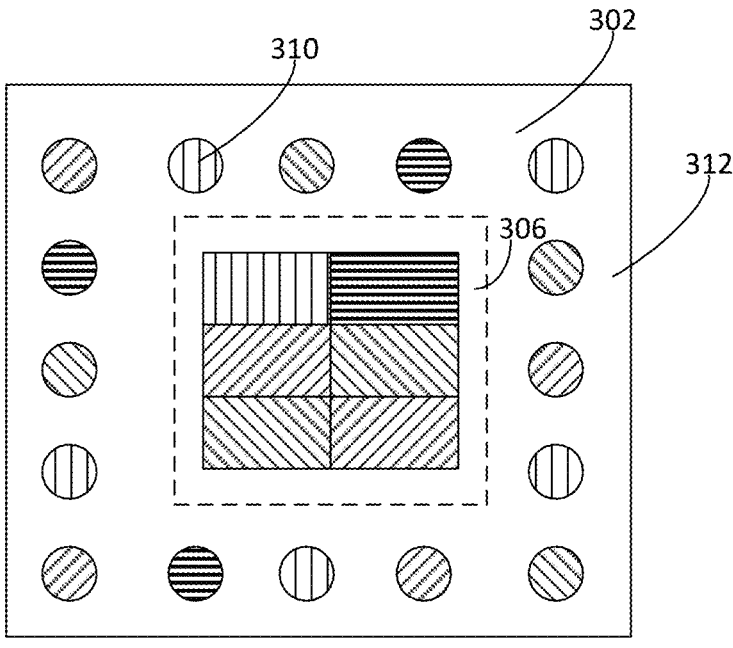
FIG. 3 is a simplified schematic diagram that shows a top view of an example integrated circuit that uses wire grid polarizers according to certain embodiments.

Turning to FIG. 3, an example of a wire grid polarizer 302 implemented in connection with an integrated circuit for PPG having a stacked first die with one or more image sensors and a second die with one or more light emitters is shown according to some embodiments.

As illustrated, wire grid polarizer 302 is applied to each TPV, such as TPV 310. In some embodiments, different TPVs may be associated with different polarization angles, as shown in FIG. 3. Selection of polarization angle may be selected based on application, e.g., various internal elements that are to be distinguished in PPG data.

As illustrated, wire grid polarizer 302 is applied to image sensors 306. It should be noted that, by applying wire grid polarizer 302 to both TPV 310 and image sensors 306, both emitted and detected light may be polarized by the same polarization angle. Different polarization angles may be applied to image sensors 306. The polarization angles applied to image sensors 306 and to the TPVs may be the same such that emitted light and detected light may be polarized by the same polarization angles.

In some embodiments, wire grid polarizer 302 may be etched away from a remaining portion 312 of a surface of a die on which image sensors 306 are included, as shown in FIG. 3. Alternatively, in some embodiments, wire grid polarizer 302 may not be etched away from remaining portion 312. In some embodiments, wire grid polarizer that is not etched away from remaining portion 312 may be used in some applications, e.g., for biasing.

In some embodiments, one or more image sensors included in an integrated circuit for PPG may be a CMOS image sensor. For example, in some embodiments, a CMOS image sensor may be a 4T CMOS active-pixel sensor, as shown in and described below in connection with FIG. 4. Such a 4T CMOS active-pixel sensor may have four transistors, including a transfer gate, a reset gate, a selection gate, and a source-follower readout transistor. Additionally or alternatively, in some embodiments, a CMOS image sensor may be a lock-in pixel. Such a lock-in pixel may include two transfer gates, each associated with a reset gate, a selection gate, and a source-follower readout transistor, as shown in and described below in connection with FIG. 5.

Each CMOS image sensor may include a pinned photodiode layer. When coupled to a transfer gate (or two transfer gates, in the case of a lock-in pixel), the pinned photodiode may allow complete charge transfer to the gate of a source-follower readout transistor (e.g., via a floating diffusion layer).

It should be noted that CMOS image sensors may be arranged in a two-dimensional array of rows and columns. In some such embodiments, CMOS image sensors in a particular row may share a reset line, such that the whole row is reset at the same time.

Figure 4:
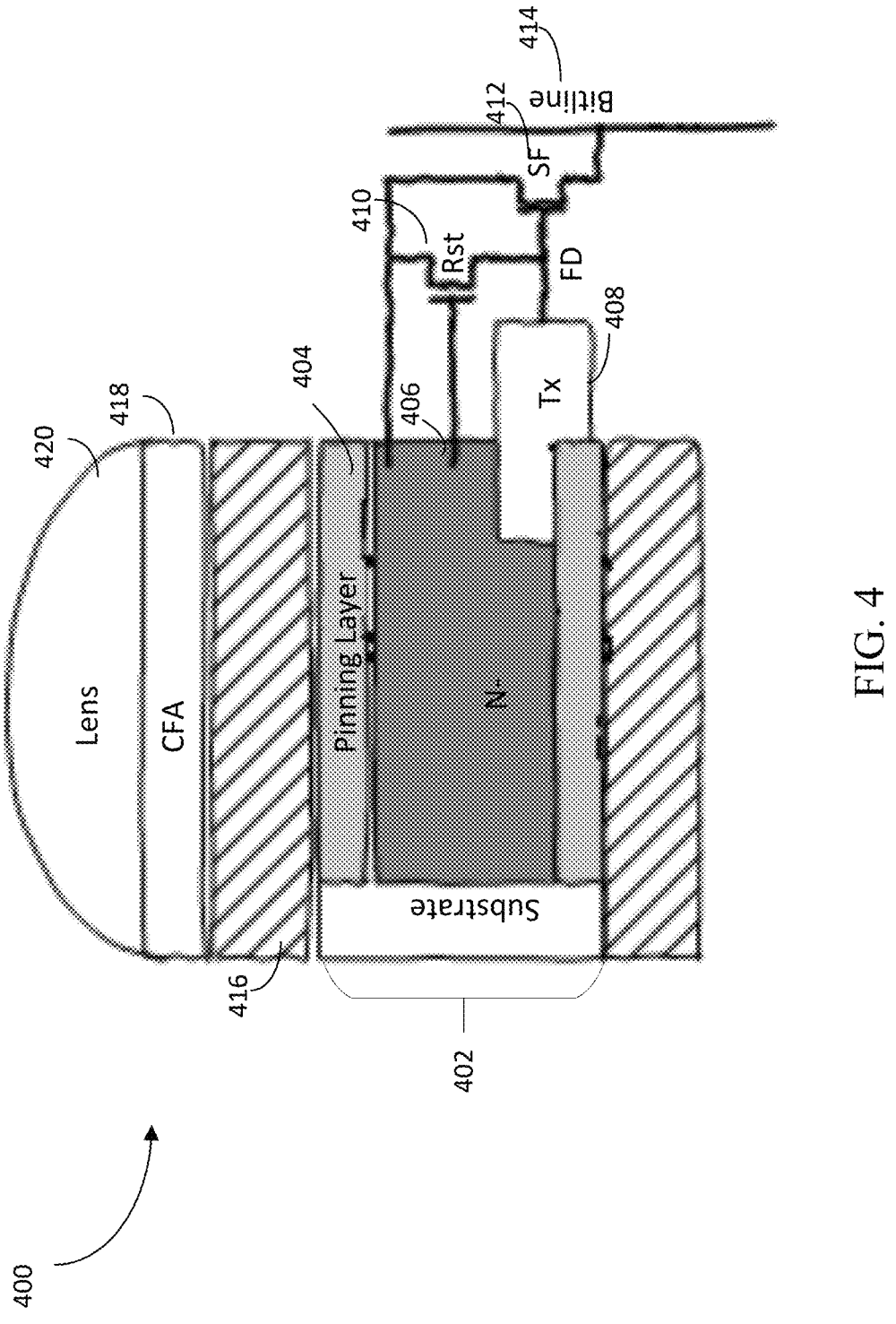
FIG. 4 is a simplified schematic diagram of an example 4T CMOS image sensor that can be used in connection with an integrated circuit for PPG according to certain embodiments.

FIG. 4 shows a simplified schematic diagram of an example 4T CMOS image sensor 400 that can be used in an integrated circuit for PPG according to some embodiments.

As illustrated, 4T CMOS image sensor 400 includes a pinned photodiode 402. Pinned photodiode 402 may include a pinning layer 404 and/or a diffusion layer 406. Diffusion layer 406 may be an N-type diffusion layer. Pinned photodiode 402 may include a substrate, which may be a P-type epitaxial substrate layer.

As illustrated, 4T CMOS image sensor 400 includes a transfer gate 408, a reset gate 410, and a source-follower readout transistor 412. Transfer gate 408 is operatively coupled to reset gate 410 and to source-follower readout transistor 412. Source-follower readout transistor 412 is operatively coupled to a bitline 414.

As shown in and described above in connection with FIG. 2, a wire grid polarizer 416 may be incorporated above pinned photodiode layer 402. For example, wire grid polarizer 416 may be above pinning layer 404.

Additionally, in some embodiments, a color filter array 418 may be used in conjunction with 4T CMOS image sensor 400. Color filter array 418 may be used to allow a monochrome 4T CMOS image sensor to detect light of various wavelengths by filtering light of any suitable wavelengths prior to incidence on the photodiode layer. An example schematic diagram of a color filter array is shown in and described below in connection with FIG. 6. Although color filter array 418 is shown above wire grid polarizer 416 in FIG. 4 (i.e., with filtration of incident light by color filter array 418 occurring prior to polarization of filtered light by wire grid polarizer 416), this is merely exemplary. For example, in some embodiments, a position of color filter array 418 and a position of wire grid polarizer 416 may be swapped.

In some embodiments, CMOS image sensor 400 may include a lens 420 for focusing light.

It should be noted that in some embodiments, wire grid polarizer 416 and/or color filter array 418 may be omitted.

Figure 5:
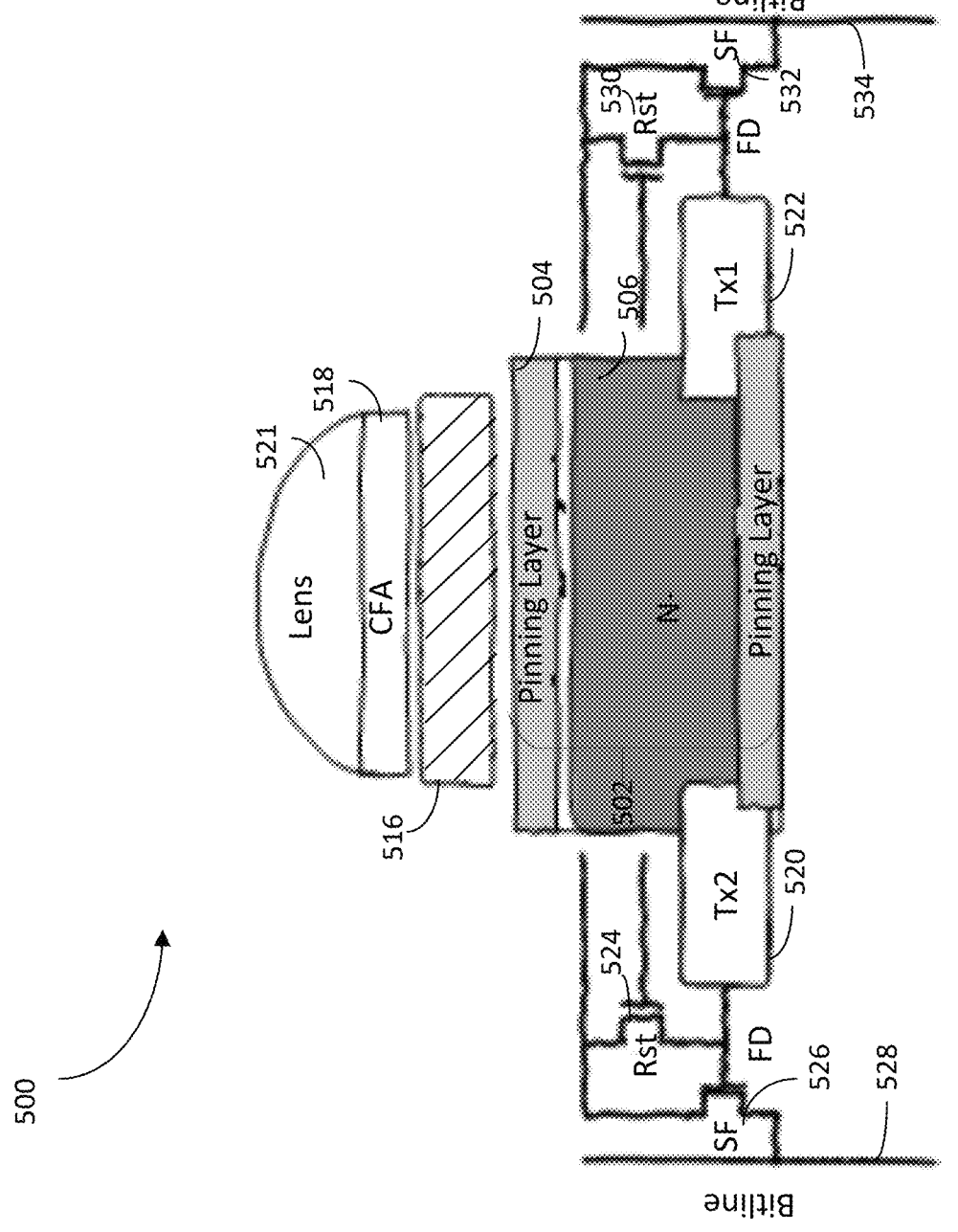
FIG. 5 is a simplified schematic diagram of an example lock-in pixel CMOS image sensor that can be used in connection with an integrated circuit for PPG according to certain embodiments.

FIG. 5 shows a simplified schematic diagram of a lock-in pixel CMOS image sensor 500 that can be used in an integrated circuit for PPG according to some embodiments.

As illustrated, lock-in pixel CMOS image sensor 500 includes a pinned photodiode 502. Pinned photodiode 502 may include a pinning layer 504 and/or a diffusion layer 506. Diffusion layer 506 may be an N-type diffusion layer. Pinned photodiode 502 may include a substrate, which may be a P-type epitaxial substrate layer.

As shown in and described above in connection with FIG. 2, a wire grid polarizer 516 may be incorporated above pinned photodiode 502. For example, wire grid polarizer 516 may be above pinning layer 504.

Additionally, in some embodiments, a color filter array 518 may be used in conjunction with lock-in pixel CMOS image sensor 500. Color filter array 518 may be used to allow a monochrome lock-in pixel CMOS image sensor to detect light of various wavelengths by filtering light of any suitable wavelengths prior to incidence on the photodiode layer. An example schematic diagram of a color filter array is shown in and described below in connection with FIG. 6. Although color filter array 518 is shown above wire grid polarizer 516 in FIG. 5 (i.e., with filtration of incident light by color filter array 518 occurring prior to polarization of filtered light by wire grid polarizer 516), this is merely exemplary. For example, in some embodiments, a position of color filter array 518 and a position of wire grid polarizer 516 may be swapped.

It should be noted that in some embodiments, wire grid polarizer 516 and/or color filter array 518 may be omitted.

In some embodiments, CMOS image sensor 500 may include a lens 521 for focusing light.

Unlike the 4T CMOS image sensor shown in FIG. 4, lock-in pixel CMOS image sensor 500 has two transfer gates, first transfer gate 520 and second transfer gate 522.

Each transfer gate may be associated with a reset gate and a source-follower readout transistor. For example, first transfer gate 520 is operatively coupled to first reset gate 524 and to first source-follower readout transistor 526. First source-follower readout transistor 526 is operatively coupled to a bitline 528. Similarly, second transfer gate 522 is operatively coupled to second reset gate 530 and to second source-follower readout transistor 532. Second source-follower readout transistor 532 is operatively coupled to a bitline 534.

In some embodiments, first transfer gate 520 and second transfer gate 522 may be used to perform quadrature sampling of samples of light detected by lock-in pixel CMOS image sensor 500. For example, in some embodiments, first transfer gate 520 may be activated and deactivated with a first waveform having a predetermined frequency corresponding to a predetermined frequency at which a light emitter is pulsed. Continuing with this example, second transfer gate 522 may be activated and deactivated with a second waveform having the same predetermined frequency as the first waveform, and out of phase with the first waveform. As a more particular example, the second waveform may be 90 degrees out of phase with the first waveform.

By performing quadrature sampling using lock-in pixel CMOS image sensor 500, a DC offset of PPG data corresponding to characteristics of reflected light captured by lock-in pixel CMOS image sensor 500 may be determined. Additionally, phase characteristics of the PPG data may be determined. Additional techniques for determining a DC offset and/or phase characteristics of PPG data using quadrature sampling are shown in and described below in connection with FIG. 7.

Figure 6:
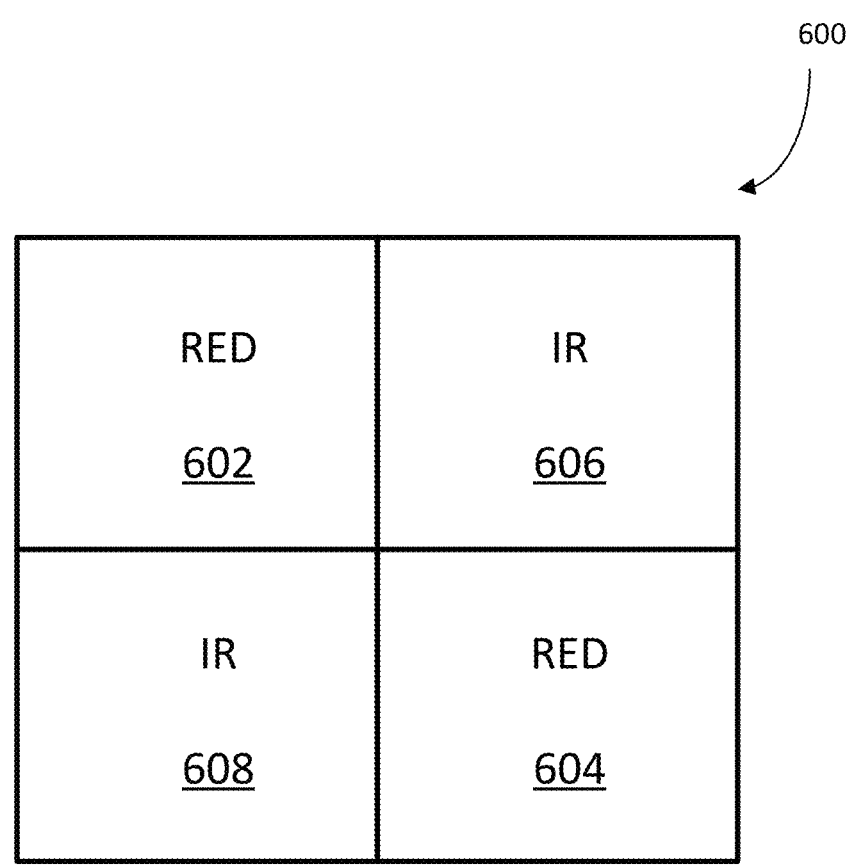
FIG. 6 is a simplified schematic diagram of an example color filter array that can be used in an integrated circuit according to certain embodiments.

FIG. 6 shows a simplified schematic diagram of a color filter array 600 that can be used in conjunction with a CMOS image sensor, such as the 4T CMOS image sensor shown in FIG. 4 and/or the lock-in pixel CMOS image sensor shown in FIG. 5, according to some embodiments.

Color filter array 600 incorporates various color filtration patterns to filter light prior to incidence on a photodiode layer of an image sensor. For example, as illustrated in FIG. 6, color filter array 600 includes red filtration patterns 602 and 604 and infrared filtration patterns 606 and 608.

Each filtration pattern may be configured to filter a particular wavelength of light. For example, red filtration patterns 602 and/or 604 may be configured to filter red light that is within a range of about 580 nanometers-700 nanometers, within a range of about 630 nanometers-680 nanometers, or the like. As another example, infrared filtration patterns 606 and/or 608 may be configured to filter infrared light that is within a range of about 870 nanometers-1000 nanometers, within a range of about 870 nanometers-970 nanometers, within a range of about 920 nanometers-970 nanometers, or the like.

It should be noted that, in some embodiments, a filtration pattern may be selected to filter wavelengths of light particularly useful for determination of various physiological characteristics based on PPG data. For example, in some embodiments, a red filtration pattern may be selected to filter light at a red wavelength at which oxygenated and deoxygenated blood show the largest difference in light absorption. As another example, in some embodiments, an infrared filtration pattern may be selected to filter light at an infrared wavelength at which oxygenated and deoxygenated blood show the larges difference in light absorption.

As described above in connection with FIG. 5, in some embodiments, a lock-in pixel CMOS image sensor that has two transfer gates may be used to determine a DC offset associated with PPG data and/or phase characteristics of PPG data. Determining the DC offset and/or the phase characteristic may allow better discrimination of reflected light from the targeted tissue versus ambient background light. For example, the DC offset may indicate ambient background light, such as detected by the image sensor while outside, from ambient indoor lighting, or the like. Continuing with this example, in some embodiments, by removing DC signal associated with the DC offset, noise associated with the ambient background can be rejected.

Figure 7:
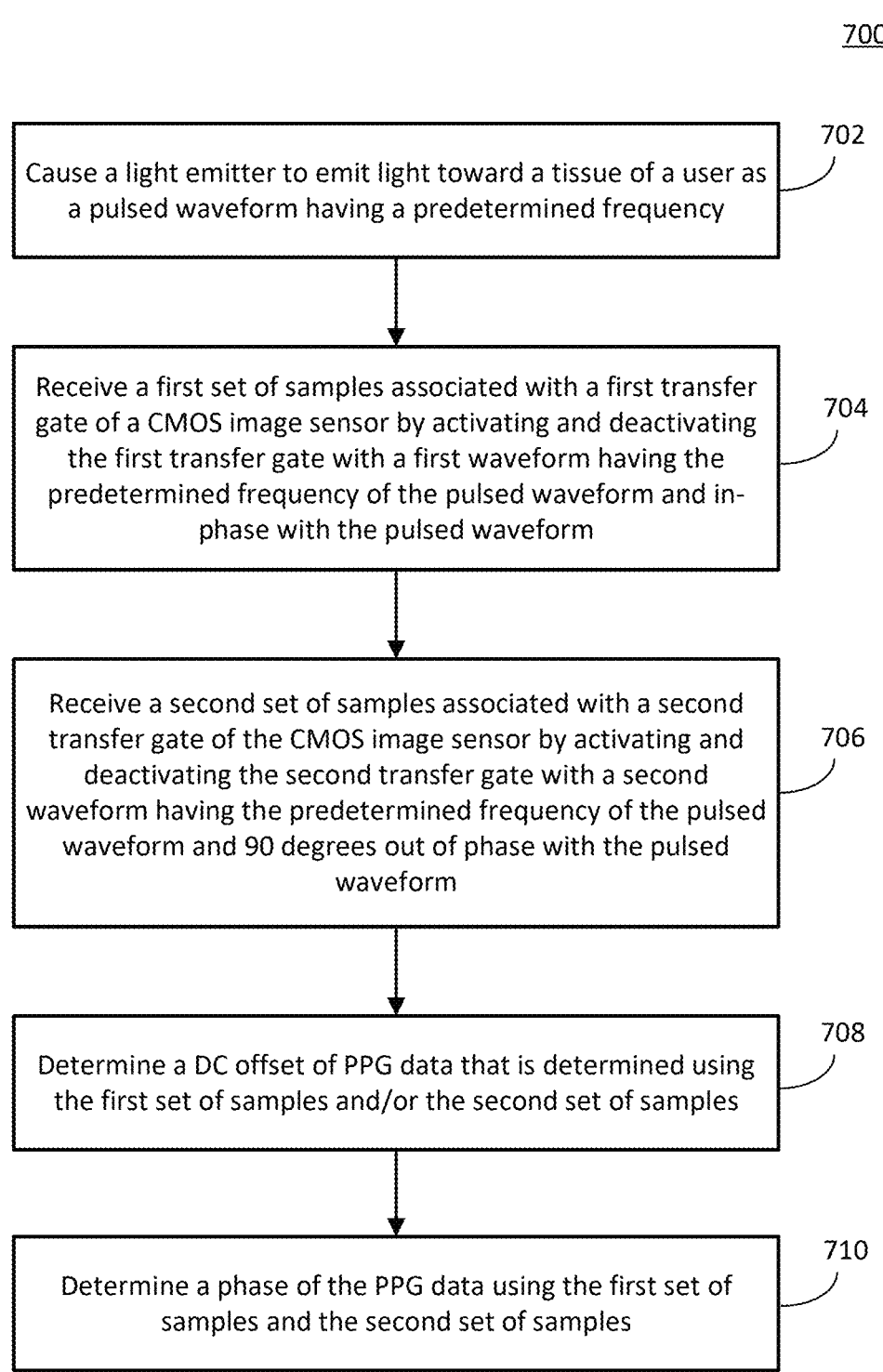
FIG. 7 is a flowchart of an example process that can be used for quadrature sampling in connection with an integrated circuit for PPG according to certain embodiments.

FIG. 7 shows a flowchart of an example process 700 for determining characteristics of PPG data using quadrature sampling of a lock-in pixel CMOS image sensor according to some embodiments. Blocks of process 700 may be implemented by a controller or processor, such as a processor shown in FIGS. 9A and/or 9B. In some embodiments, such a controller or processor may be implemented as part of an ASIC.

At 702, process 700 can cause a light emitter to emit light toward a tissue of a user as a pulsed waveform having a predetermined frequency. The light emitter may be an LED, a VCSEL, an e-VCSEL, or the like. In some embodiments, process 700 may cause multiple light emitters (e.g., five light emitters, ten light emitters, or the like) to emit light toward the tissue of the user. In some embodiments, each light emitter may be associated with the pulsed waveform having the predetermined frequency. The light emitter may emit light of any suitable wavelengths, such as in a red wavelength (e.g. in a range of about 625 nanometers-740 nanometers) and/or in an infrared wavelength (e.g., in a range of about 760 nanometers-1000 nanometers), or any combination thereof.

At 704, process 700 can receive a first set of samples associated with a first transfer gate of a lock-in pixel CMOS image sensor. The first set of samples may be received by activating and deactivating the first transfer gate with a first waveform. The first set of samples may be obtained from a bitline coupled to a source-follower readout transistor associated with the first transfer gate, as shown in and described above in connection with FIG. 5. In some embodiments, the first waveform with which the first transfer gate is activated and deactivated may have the same predetermined frequency as the predetermined frequency of the pulsed waveform of the light emitter. In some embodiments, the first waveform may be in-phase with the pulsed waveform.

At 706, process 700 can receive a second set of samples associated with a second transfer gate of the lock-in pixel CMOS image sensor. The second set of samples may be received by activating and deactivating the second transfer gate with a second waveform. The second set of samples may be obtained by a bitline coupled to a source-follower readout transistor associated with the second transfer gate, as shown in and described above in connection with FIG. 5. In some embodiments, the second waveform with which the second transfer gate is activated and deactivated may have the same predetermined frequency with which the first transfer gate is activated and deactivated and/or the same predetermined frequency as the predetermined frequency of the pulsed waveform of the light emitter. In some embodiments, the second waveform may be out-of-phase (e.g., about 90 degrees out-of-phase) with the first waveform associated with the first transfer gate and/or out-of-phase (e.g., about 90 degrees out-of-phase) with the pulsed waveform of the light emitter.

It should be noted that samples in the first set of samples and samples in the second set of samples each indicate characteristics of light reflected from the tissue of the user or reflected from internal body elements of the user that have been captured by the lock-in CMOS image sensor. The characteristics of the reflected light may be used to determine PPG data for the user. The PPG data may be proportional to an amount of blood flowing through vessels within proximity of the tissue toward which light was emitted at block 702. In some embodiments, the PPG data may be used to determine various physiological characteristics of the user, such as heart rate, heart rate variability, oxygen saturation, or the like. More detailed techniques for determining PPG data and/or physiological characteristics of the user based on samples obtained by an image sensor are shown in and described below in connection with FIG. 8.

At 708, process 700 can determine a DC offset of PPG data that is determined using the first set of samples and the second set of samples. For example, in some embodiments, the DC offset may be determined based on two samples that are 180 degrees out of phase with each other. For example, in some embodiments, the two samples may be two samples of the first set of samples that correspond to time points of the first waveform that are 180 degrees apart. As another example, in some embodiments, the two samples may be two samples of the second set of samples that correspond to time points of the second waveform that are 180 degrees apart.

In some embodiments, the DC offset may be obtained by averaging the values of the two samples. In some embodiments, a DC offset may be determined using more than two samples. For example, in some embodiments, a DC offset may be determined as an average of averages (e.g., an average of averages of 180 degree out of phase samples).

At 710, process 700 can determine phase characteristics of the PPG data using the first set of samples and the second set of samples. For example, in some embodiments, the phase characteristics can be determined based on a first sample from the first set of samples and a second sample from the second set of samples that are 90 degrees apart. Continuing with this example, in some embodiments, I and Q components can be determined from the first sample and the second sample. As a more particular example, the I component can be determined by subtracting the DC offset determined at block 708 from the first sample. Similarly, the Q component can be determined by subtracting the DC offset determined at block 708 from the second sample. In some embodiments, the phase characteristics can be determined based on a ratio of the I component to the Q component. For example, in some embodiments, the phase can be determined by:

$$\theta = \tan^{-1}\frac{I}{Q}.$$

It should be noted that, in some embodiments, the phase characteristics may represent multiple phase estimations. For example, multiple phase estimations may each be determined using a sample from the first set of samples and a corresponding sample from the second set of samples that is 90 degrees apart from the sample from the first set of samples, as described above. Continuing with this example, the multiple phase estimations may then be averaged together to determine the phase characteristics such that the phase characteristics indicate an average phase associated with the PPG data over a time window spanned by the multiple phase estimations.

FIG. 8 shows a flowchart of a process 800 for determining characteristics of PPG data using according to some embodiments. Blocks of process 800 may be implemented by a controller or processor, such as a processor shown in FIGS. 9A and/or 9B. In some embodiments, such a controller or processor may be implemented as part of an ASIC. It should be noted that process 800 may be implemented with any suitable image sensor, such as the 4T CMOS image sensor shown in and described above in connection with FIG. 4, the lock-in pixel CMOS image sensor shown in and described above in connection with FIG. 5, or the like.

At 802, process 800 can cause a light emitter to emit light toward a tissue of a user. The light emitter may be an LED, a VCSEL, and e-VCSEL, or the like. In some embodiments, process 800 may cause multiple light emitters (e.g., five light emitters, ten light emitters, or the like) to emit light toward the tissue of the user. In some embodiments, the light may be emitted as a pulsed waveform having a predetermined frequency. The light emitter may emit light of any suitable wavelengths, such as in a red wavelength (e.g. in a range of about 625 nanometers-740 nanometers) and/or in an infrared wavelength (e.g., in a range of about 760 nanometers-1000 nanometers), or any combination thereof.

At 804, process 800 may obtain samples of reflected light captured by at least one image sensor. The reflected light may be reflected off external tissue (e.g., an external layer of skin) of the user, or off of one or more internal elements within a body of the user proximate to the tissue. The one or more internal elements may include blood vessels (e.g., capillaries, arterioles, veins, arteries, or the like), bone, internal layers of skin, or the like.

The samples may be obtained using any suitable type of image sensor, such as a 4T CMOS image sensor as shown in and described above in connection with FIG. 4, a lock-in pixel CMOS image sensor as shown in and described above in connection with FIG. 5, or the like. The samples may be obtained at a sampling frequency and over any suitable time duration (e.g., 100 milliseconds, 500 milliseconds, or the like). Example values of sampling frequency may be 100 MHz, 200 MHz, 300 MHz, or the like.

It should be noted that, as described above in connection with FIGS. 4 and 5, a color filter array may be used such that that reflected light is filtered prior to being captured by the image sensor(s). For example, in some embodiments, reflected light may be filtered to a red wavelength of interest (e.g., about 650 nanometers, about 660 nanometers, or the like) and to an infrared wavelength of interest (e.g., of about 930 nanometers, 940 nanometers, or the like). Accordingly, the obtained samples may indicate reflected light having wavelengths corresponding to the wavelengths of interest associated with the color filter array. For example, a first subset of the obtained samples may correspond to reflected light in the red wavelength, and a second subset of the obtained samples may correspond to reflected light in the infrared wavelength.

At 806, process 800 may determine one or more characteristics of the reflected light based on the obtained samples. For example, in some embodiments, process 800 may determine an amount of reflected light at different wavelengths. As another example, in some embodiments, process 800 may determine AC and DC components of the obtained samples. As a more particular example, in some embodiments, process 800 may determine AC and DC components of samples of reflected light in the red wavelength range (referred to herein as AC'red and D) C'red) and AC and DC components of samples of reflected light in the infrared wavelength range (referred to herein as $AC_{IR}$ and $DC_{IR}$).

At 810, process 800 may determine PPG data based on the one or more characteristics of the reflected light. The PPG data may correspond to the obtained samples that have been processed in any suitable manner, for example to remove noise (e.g., based on DC offset or phase characteristics, as described above in connection with FIG. 7). The PPG data may indicate a volume of blood flow as a function of time within the tissue of the user. Accordingly, a waveform of the PPG data may be periodic with a periodicity that indicates a heart rate of the user.

It should be noted that, in some embodiments, in instances in which a wire grid polarizer is used to polarize detected light, the one or more characteristics of the reflected light may be determined based on polarizations of the detected light. For example, in some embodiments, process 800 may identify one or more subsets of the samples obtained at block 804 as reflected off of a internal body element (e.g., a particular skin layer, a blood vessel, bone, or the like) based on a polarization associated with each subset. Continuing with this example, in some embodiments, process 800 may determine the PPG data using particular subsets of samples corresponding to particular body elements (e.g., a blood vessel), and not using other subsets of samples corresponding to other body elements (e.g., skin).

At 812, process 800 may determine physiological characteristics of the user based on the PPG data. For example, in some embodiments, the physiological characteristics may include a heart rate of the user. In some embodiments, the heart rate of the user may be calculated based on a periodicity of the PPG data determined at block 810. For example, in some embodiments, the heart rate may be calculated as an inverse of an inter-period time interval. In some embodiments, other physiological characteristics may be determined based on the heart rate of the user, such as a heart rate variability.

As another example, in some embodiments, an oxygen saturation level of the user may be determined based on the PPG data determined at block 810 and/or based on the characteristics of the reflected light determined at block 808. For example, in some embodiments, a perfusion index percentage (referred to herein as R) may be calculated based on the AC and DC components of the reflected light in the red wavelength and based on the AC and DC components of the reflected light in the infrared wavelength. As a more particular example, the perfusion index percentage may be calculated as:

$$R = \frac{\frac{AC_{red}}{DC_{red}}}{\frac{AC_{IR}}{DC_{IR}}}.$$

Continuing with this more particular example, in some embodiments, the oxygen saturation can be based on a calibration that maps the perfusion index percentage R to the oxygen saturation level. In some embodiments, such a calibration may be device-dependent.

It should be noted that one or more of the physiological characteristics may be determined by using the PPG data as an input to a trained machine learning model that has been trained to output one or more physiological characteristics.

In some embodiments, an indication of the physiological characteristics may be presented to the user, such as in a user interface. Additionally or alternatively, in some embodiments, indications of the physiological characteristics may be stored, for example, in memory of user device and/or in a remote memory (e.g., of a server).

Figure 9A:
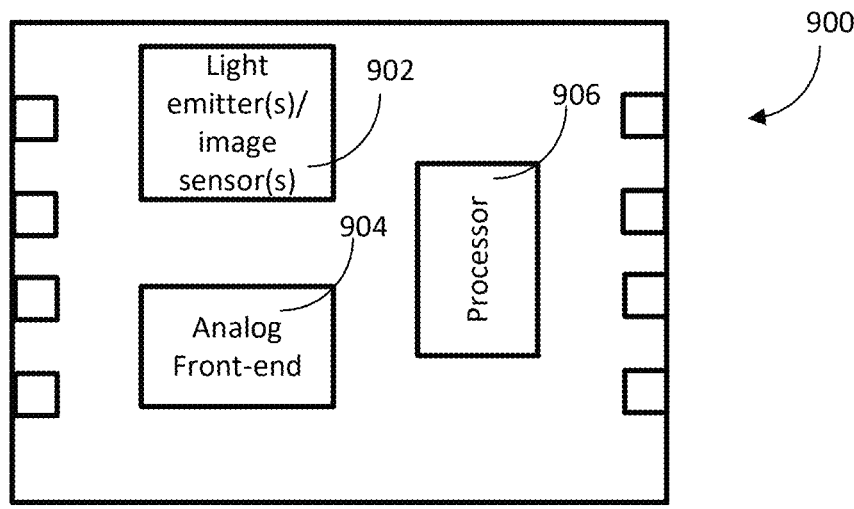
FIG. 9A is a simplified schematic diagram that shows components of an example integrated circuit package for PPG in a side by side configuration according to certain embodiments.

In some embodiments, an integrated circuit that includes one or more light emitters and one or more image sensors (e.g., stacked vertically, as shown in and described above in connection with FIGS. 1A, 1B, and 3) may be integrated into a package that includes an analog front-end and/or one or more processor(s). In some embodiments, the package may include the light emitter(s)/light sensor(s), analog front-end, and/or processor(s) laid out in a side-by-side configuration, as shown in FIG. 9A. In some embodiments, the package may include the light emitter(s)/image sensor(s), analog front-end, and/or processor(s) laid out in a vertically stacked configuration, as shown in FIG. 9B.

It should be noted that, in some embodiments, individual components of an integrated circuit package may be interconnected using a controlled collapse chip connection, or flip chip, technique. For example, in some embodiments, an integrated circuit that includes a first die associated with one or more image sensors and a second die associated with one or more light emitters may be interconnected with the integrated circuit package using a flip chip technique. Continuing with this example, in some embodiments, the integrated circuit may be fabricated with solder bumps deposited (e.g., using wafer bumping, or the like) on either the first die or the second die. Continuing still further with this example, in some embodiments, the integrated circuit may be flipped over onto the integrated circuit package such that the solder bumps rest on a surface of the integrated circuit package and are in alignment with matching pads on the integrated circuit package. In some embodiments, the solder bumps can then be re-melted (e.g., using hot airflow, or the like). In some embodiments, the mounted integrated circuit may be underfilled.

Figure 9B:
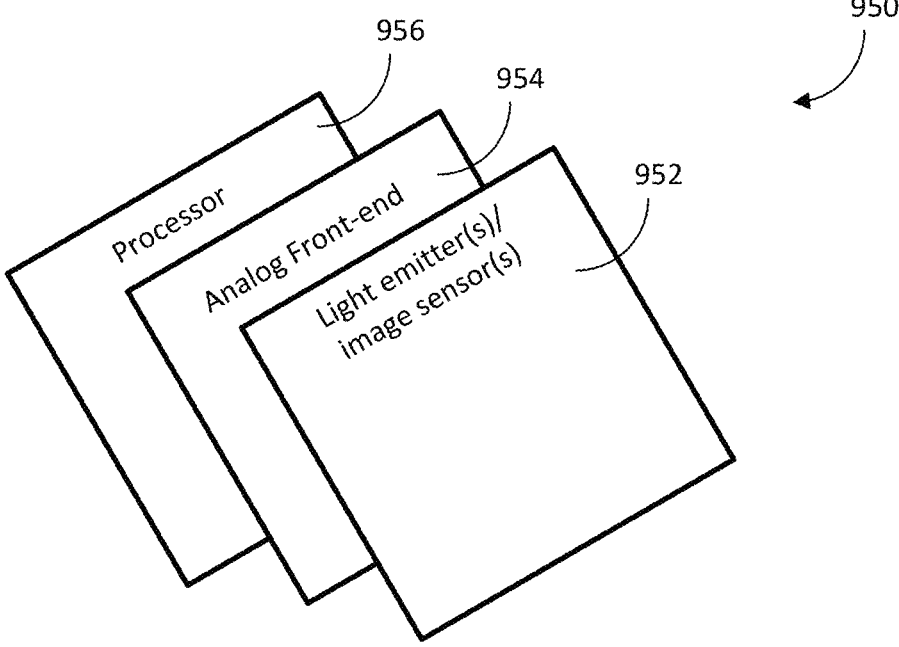
FIG. 9B is a simplified schematic diagram that shows components of an example integrated circuit package for PPG in a stacked configuration according to certain embodiments.

It should be noted that, in some embodiments, an integrated circuit package (e.g., as shown in FIG. 9A or 9B) may be configured to communicate with another device. For example, in an instance in which an integrated circuit package is incorporated into a wearable device (e.g., an AR/VR headset, a smart watch, or the like), the integrated circuit package may be configured to communicate with the wearable device. As a more particular example, in some embodiments, the wearable device may be configured to present indications of PPG data or physiological characteristics of a user determined by a processor of the integrated circuit package.

FIG. 9A shows an example architecture for an integrated circuit package 900 for determining PPG data based on detected light characteristics in which different modules are laid out side by side according to some embodiments. As illustrated, integrated circuit package 900 includes one or more light emitter(s)/image sensor(s) 902, an analog front-end 904, and a processor 906.

Light emitter(s)/image sensor(s) 902 may include one or more light emitters and one or more image sensors in a stacked configuration, as shown in and described above in connection with FIGS. 1A and 1B. In some embodiments, image sensor(s) of light emitter(s)/image sensor(s) 902 may be a CMOS image sensor, such as a 4T CMOS image sensor as shown in and described above in connection with FIG. 4, a lock-in pixel CMOS image sensor as shown in and described above in connection with FIG. 5, or the like.

Analog front-end 904 may include any suitable components or modules for amplifying signals from image sensor(s) 902 and/or digitizing the signals. For example, in some embodiments, analog front-end 904 may be configured to apply a gain to signals generated by image sensor(s) 902. Such a gain may be applied using an amplifier. As another example, in some embodiments, analog front-end 904 may be configured to digitize signals generated by image sensor(s) 902 and/or amplified signals generated by image sensor(s) 902. As a more particular example, in some embodiments analog front-end 904 may include an analog to digital converter (ADC) that digitizes signals generated by light emitter(s)/image sensor(s) 902 and/or amplified signals amplified by an amplifier of analog front-end 904. A specific example of an analog front-end that may be used is ADS130E08 made by TEXAS INSTRUMENTS. It should be noted that, in some embodiments, analog front-end 904 may not include an ADC. In some such embodiments, digitizing may be performed by processor 906.

Processor 906 may be configured to receive signals that indicate light detected by image sensor(s) 902 and determine PPG data and/or physiological characteristics indicated in the PPG data based on the received signals. In some embodiments, processor 906 may be configured to control one or more light emitters. In some embodiments, processor 906 may be configured to implement the blocks of process 700 of FIG. 7 and/or of process 800 of FIG. 8. In some embodiments, processor 906 may be part of an application specific integrated circuit (ASIC). In some embodiments, processor 906 may have an ARM architecture, an x86 architecture, a custom-designed architecture, or the like.

It should be noted that integrated circuit package 900 can include any other components or modules not shown in FIG. 9A. For example, in some embodiments, processor 906 may be associated with a memory. As a more particular example, in an instance in which processor 906 is implemented in an ASIC, the ASIC may additionally include one or more memories. In some embodiments, measurements from image sensor(s) may be stored in the memory. Additionally or alternatively, in some embodiments, PPG data or physiological characteristics of a user generated by processor 906 may be stored in the memory. Such a memory may be volatile, such as static random access memory (SRAM) and/or dynamic random access memory (DRAM) and/or non-volatile, such as read-only memory (ROM), flash memory, and the like. Furthermore, such a memory may include removable storage devices, such as secure digital (SD) cards. The memory may provide storage of computer-readable instructions, data structures, program modules, and other data associated with processor 906. In some embodiments, the memory may be distributed into different hardware modules. A set of instructions and/or code might be stored on the memory. The instructions might take the form of executable code that may be executable by processor 906.

FIG. 9B shows an example architecture for an integrated circuit package 950 for determining PPG data based on detected light characteristics in which different modules are stacked according to some embodiments. As illustrated, integrated circuit package 950 includes one or more light emitter(s)/image sensor(s) 952, an analog front-end 954, and a processor 956.

Light emitter(s)/image sensor(s) 952 may include one or more light emitters and one or more image sensors in a stacked configuration, as shown in and described above in connection with FIGS. 1A and 1B. In some embodiments, image sensor(s) of light emitter(s)/image sensor(s) 952 may be a CMOS image sensor, such as a 4T CMOS image sensor as shown in and described above in connection with FIG. 4, a lock-in pixel CMOS image sensor as shown in and described above in connection with FIG. 5, or the like.

Analog front-end 954 may include any suitable components or modules for amplifying signals from image sensor(s) 952 and/or digitizing the signals. For example, in some embodiments, analog front-end 954 may be configured to apply a gain to signals generated by image sensor(s) 952. Such a gain may be applied using an amplifier. As another example, in some embodiments, analog front-end 954 may be configured to digitize signals generated by image sensor(s) 952 and/or amplified signals generated by image sensor(s) 952. As a more particular example, in some embodiments analog front-end 954 may include an analog to digital converter (ADC) that digitizes signals generated by light emitter(s)/image sensor(s) 952 and/or amplified signals amplified by an amplifier of analog front-end 954. A specific example of an analog front-end that may be used is ADS130E08 made by TEXAS INSTRUMENTS. It should be noted that, in some embodiments, analog front-end 954 may not include an ADC. In some such embodiments, digitizing may be performed by processor 956.

Processor 956 may be configured to receive signals that indicate light detected by image sensor(s) 952 and determine PPG data and/or physiological characteristics indicated in the PPG data based on the received signals. In some embodiments, processor 956 may be configured to control one or more light emitters. In some embodiments, processor 956 may be configured to implement the blocks of process 700 of FIG. 7 and/or of process 800 of FIG. 8. In some embodiments, processor 956 may be part of an application specific integrated circuit (ASIC). In some embodiments, processor 956 may have an ARM architecture, an x86 architecture, a custom-designed architecture, or the like.

It should be noted that integrated circuit package 950 can include any other components or modules not shown in FIG. 9B. For example, in some embodiments, processor 956 may be associated with a memory. As a more particular example, in an instance in which processor 956 is implemented in an ASIC, the ASIC may additionally include one or more memories. In some embodiments, measurements from image sensor(s) may be stored in the memory. Additionally or alternatively, in some embodiments, PPG data or physiological characteristics of a user generated by processor 956 may be stored in the memory. Such a memory may be volatile, such as static random access memory (SRAM) and/or dynamic random access memory (DRAM) and/or non-volatile, such as read-only memory (ROM), flash memory, and the like. Furthermore, such a memory may include removable storage devices, such as secure digital (SD) cards. The memory may provide storage of computer-readable instructions, data structures, program modules, and other data associated with processor 956. In some embodiments, the memory may be distributed into different hardware modules. A set of instructions and/or code might be stored on the memory. The instructions might take the form of executable code that may be executable by processor 956

Embodiments disclosed herein may be used to implement components of an artificial reality system or may be implemented in conjunction with an artificial reality system. Artificial reality is a form of reality that has been adjusted in some manner before presentation to a user, which may include, for example, a virtual reality, an augmented reality, a mixed reality, a hybrid reality, or some combination and/or derivatives thereof. Artificial reality content may include completely generated content or generated content combined with captured (e.g., real-world) content. The artificial reality content may include video, audio, haptic feedback, or some combination thereof, and any of which may be presented in a single channel or in multiple channels (such as stereo video that produces a three-dimensional effect to the viewer). Additionally, in some embodiments, artificial reality may also be associated with applications, products, accessories, services, or some combination thereof, that are used to, for example, create content in an artificial reality and/or are otherwise used in (e.g., perform activities in) an artificial reality. The artificial reality system that provides the artificial reality content may be implemented on various platforms, including an HMD connected to a host computer system, a standalone HMD, a mobile device or computing system, or any other hardware platform capable of providing artificial reality content to one or more viewers.

The methods, systems, and devices discussed above are examples. Various embodiments may omit, substitute, or add various procedures or components as appropriate. For instance, in alternative configurations, the methods described may be performed in an order different from that described, and/or various stages may be added, omitted, and/or combined. Also, features described with respect to certain embodiments may be combined in various other embodiments. Different aspects and elements of the embodiments may be combined in a similar manner. Also, technology evolves and, thus, many of the elements are examples that do not limit the scope of the disclosure to those specific examples.

Specific details are given in the description to provide a thorough understanding of the embodiments. However, embodiments may be practiced without these specific details. For example, well-known circuits, processes, systems, structures, and techniques have been shown without unnecessary detail in order to avoid obscuring the embodiments. This description provides example embodiments only, and is not intended to limit the scope, applicability, or configuration of the invention. Rather, the preceding description of the embodiments will provide those skilled in the art with an enabling description for implementing various embodiments. Various changes may be made in the function and arrangement of elements without departing from the spirit and scope of the present disclosure.

Also, some embodiments were described as processes depicted as flow diagrams or block diagrams. Although each may describe the operations as a sequential process, many of the operations may be performed in parallel or concurrently. In addition, the order of the operations may be rearranged. A process may have additional steps not included in the figure. Furthermore, embodiments of the methods may be implemented by hardware, software, firmware, middleware, microcode, hardware description languages, or any combination thereof. When implemented in software, firmware, middleware, or microcode, the program code or code segments to perform the associated tasks may be stored in a computer-readable medium such as a storage medium. Processors may perform the associated tasks.

It will be apparent to those skilled in the art that substantial variations may be made in accordance with specific requirements. For example, customized or special-purpose hardware might also be used, and/or particular elements might be implemented in hardware, software (including portable software, such as applets, etc.), or both. Further, connection to other computing devices such as network input/output devices may be employed.

With reference to the appended figures, components that can include memory can include non-transitory machine-readable media. The term "machine-readable medium" and "computer-readable medium" may refer to any storage medium that participates in providing data that causes a machine to operate in a specific fashion. In embodiments provided hereinabove, various machine-readable media might be involved in providing instructions/code to processing units and/or other device(s) for execution. Additionally or alternatively, the machine-readable media might be used to store and/or carry such instructions/code. In many implementations, a computer-readable medium is a physical and/or tangible storage medium. Such a medium may take many forms, including, but not limited to, non-volatile media, volatile media, and transmission media. Common forms of computer-readable media include, for example, magnetic and/or optical media such as compact disk (CD) or digital versatile disk (DVD), punch cards, paper tape, any other physical medium with patterns of holes, a RAM, a programmable read-only memory (PROM), an erasable programmable read-only memory (EPROM), a FLASH-EPROM, any other memory chip or cartridge, a carrier wave as described hereinafter, or any other medium from which a computer can read instructions and/or code. A computer program product may include code and/or machine-executable instructions that may represent a procedure, a function, a subprogram, a program, a routine, an application (App), a subroutine, a module, a software package, a class, or any combination of instructions, data structures, or program statements.

Those of skill in the art will appreciate that information and signals used to communicate the messages described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Terms, "and" and "or" as used herein, may include a variety of meanings that are also expected to depend at least in part upon the context in which such terms are used. Typically, "or" if used to associate a list, such as A, B, or C, is intended to mean A, B, and C, here used in the inclusive sense, as well as A, B, or C, here used in the exclusive sense. In addition, the term "one or more" as used herein may be used to describe any feature, structure, or characteristic in the singular or may be used to describe some combination of features, structures, or characteristics. However, it should be noted that this is merely an illustrative example and claimed subject matter is not limited to this example. Furthermore, the term "at least one of" if used to associate a list, such as A, B, or C, can be interpreted to mean any combination of A, B, and/or C, such as A, AB, AC, BC, AA, ABC, AAB, AABBCCC, etc.

Further, while certain embodiments have been described using a particular combination of hardware and software, it should be recognized that other combinations of hardware and software are also possible. Certain embodiments may be implemented only in hardware, or only in software, or using combinations thereof. In one example, software may be implemented with a computer program product containing computer program code or instructions executable by one or more processors for performing any or all of the steps, operations, or processes described in this disclosure, where the computer program may be stored on a non-transitory computer readable medium. The various processes described herein can be implemented on the same processor or different processors in any combination.

Where devices, systems, components or modules are described as being configured to perform certain operations or functions, such configuration can be accomplished, for example, by designing electronic circuits to perform the operation, by programming programmable electronic circuits (such as microprocessors) to perform the operation such as by executing computer instructions or code, or processors or cores programmed to execute code or instructions stored on a non-transitory memory medium, or any combination thereof. Processes can communicate using a variety of techniques, including, but not limited to, conventional techniques for inter-process communications, and different pairs of processes may use different techniques, or the same pair of processes may use different techniques at different times.

The specification and drawings are, accordingly, to be regarded in an illustrative rather than a restrictive sense. It will, however, be evident that additions, subtractions, deletions, and other modifications and changes may be made thereunto without departing from the broader spirit and scope as set forth in the claims. Thus, although specific embodiments have been described, these are not intended to be limiting. Various modifications and equivalents are within the scope of the following claims.

What is claimed is:

1. An apparatus, comprising:
a first die comprising one or more image sensors;
a second die comprising one or more light emitters;
one or more through package vias (TPVs), wherein a TPV of the one or more TPVs is configured to allow light emitted from at least one light emitter of the one or more light emitters to pass through the first die; and a controller configured to:

cause the at least one light emitter to emit light, through the TPV of the one or more TPVs, toward a tissue of a user;

determine one or more characteristics of reflected light captured by at least one image sensor of the one or more image sensors; and determine photoplethysmography (PPG) data for the user based on the determined one or more characteristics of the reflected light.

2. The apparatus of claim 1, wherein the TPV of the one or more TPVs is filled with a high-index light guide material such that the TPV couples light from the at least one light emitter.

3. The apparatus of claim 1, further comprising a wire grid polarizer above the first die.

4. The apparatus of claim 3, wherein the wire grid polarizer comprises a plurality of orientations.

5. The apparatus of claim 4, wherein the plurality of orientations are each arranged on a different portion of the wire grid polarizer.

6. The apparatus of claim 1, where the one or more light emitters comprise one or more vertical cavity surface-emitting lasers (VCSELs).

7. The apparatus of claim 1, wherein at least a subset of the one or more light emitters emit light in an infrared wavelength.

8. The apparatus of claim 7, wherein the infrared wavelength is within a range of about 870 nanometers-970 nanometers.

9. The apparatus of claim 1, wherein at least a subset of the one or more light emitters emit light in a red wavelength.

10. The apparatus of claim 9, wherein the red wavelength is within a range of about 630 nanometers to 680 nanometers.

11. The apparatus of claim 1, wherein the one or more image sensors comprise one or more CMOS image sensors.

12. The apparatus of claim 11, wherein a CMOS image sensor of the one or more CMOS image sensors comprises two transfer gates.

13. The apparatus of claim 1, wherein the controller is further configured to:

receive a first set of samples by activating and deactivating a first image sensor of the one or more image sensors with a first waveform having a predetermined frequency and in phase with a pulsed waveform; and receive a second set of samples by activating and deactivating the first image sensor with a second waveform having the predetermined frequency and out of phase with the pulsed waveform.

14. The apparatus of claim 13, wherein the controller is further configured to determine a DC offset of the PPG data based on an average of two samples of the first set of samples.

15. The apparatus of claim 13, wherein the controller is further configured to determine a phase of the PPG data based on a ratio of a sample of the first set of samples to a sample of the second set of samples.

16. The apparatus of claim 11, wherein a CMOS image sensor of the one or more CMOS image sensors is a 4T CMOS image sensor.

17. A method, comprising:

causing at least one light emitter to emit light toward a tissue of a user, wherein a first die comprises the at least one light emitter, and wherein light emitted from the at least one light emitter passes through one or more through package vias (TPVs) and through a second die that comprises one or more image sensors;

determining one or more characteristics of reflected light captured by at least one image sensor of the one or more image sensors; and determining photoplethysmography (PPG) data for the user based on the determined one or more characteristics of the reflected light.

18. The method of claim 17, wherein causing the one or more light emitters to emit light towards the tissue of the user comprises causing the one or more light emitters to emit light as a pulsed waveform having a predetermined frequency, and wherein the method further comprises:

receiving a first set of samples associated with a first transfer gate of the two transfer gates by activating and deactivating the first transfer gate of the two transfer gates with a first waveform having the predetermined frequency and in phase with the pulsed waveform; and receiving a second set of samples associated with a second transfer gate of the two transfer gates by activating and deactivating the second transfer gate of the two transfer gates with a second waveform having the predetermined frequency and 90 degrees out of phase with the pulsed waveform.

19. The method of claim 18, further comprising determining a DC offset of the PPG data based on an average of two samples of the first set of samples.

20. The method of claim 18, further comprising determining a phase of the PPG data based on a ratio of a sample of the first set of samples to a sample of the second set of samples.

21. An apparatus, comprising:

means for causing at least one light emitter to emit light toward a tissue of a user, wherein a first die comprises the at least one light emitter, and wherein light emitted from the at least one light emitter passes through one or more through package vias (TPVs) and through a second die that comprises one or more image sensors;

means for determining one or more characteristics of reflected light captured by at least one image sensor of the one or more image sensors; and means for determining photoplethysmography (PPG) data for the user based on the determined one or more characteristics of the reflected light.

22. A non-transitory computer-readable medium storing instructions for:

causing at least one light emitter to emit light toward a tissue of a user, wherein a first die comprises the at least one light emitter, and wherein light emitted from the at least one light emitter passes through one or more through package vias (TPVs) and through a second die that comprises one or more image sensors;

determining one or more characteristics of reflected light captured by at least one image sensor of the one or more image sensors; and determining photoplethysmography (PPG) data for the user based on the determined one or more characteristics of the reflected light.

\* \* \* \* \*